(12) United States Patent
Darbandi et al.

(10) Patent No.: US 12,171,965 B2
(45) Date of Patent: Dec. 24, 2024

(54) SYSTEMS, CATHETERS, AND METHODS FOR TREATING ALONG THE CENTRAL NERVOUS SYSTEM

(71) Applicant: MINNETRONIX NEURO, INC., St. Paul, MN (US)

(72) Inventors: Bejan Michael Darbandi, Chanhassen, MN (US); Aaron R. McCabe, Edina, MN (US)

(73) Assignee: MINNETRONIX NEURO, INC., St. Paul, MN (US)

( * ) Notice: Subject to any disclaimer, the term of this patent is extended or adjusted under 35 U.S.C. 154(b) by 287 days.

(21) Appl. No.: 17/166,637

(22) Filed: Feb. 3, 2021

(65) Prior Publication Data

US 2021/0236781 A1    Aug. 5, 2021

Related U.S. Application Data

(60) Provisional application No. 62/969,632, filed on Feb. 3, 2020.

(51) Int. Cl.
*A61M 27/00* (2006.01)

(52) U.S. Cl.
CPC ... *A61M 27/006* (2013.01); *A61M 2202/0464* (2013.01); *A61M 2205/75* (2013.01)

(58) Field of Classification Search
CPC .............. A61M 1/88; A61M 1/884; A61M 2202/0464; A61M 2205/12;
(Continued)

(56) References Cited

U.S. PATENT DOCUMENTS

| | | | |
|---|---|---|---|
| 4,500,311 A | | 2/1985 | Redmond et al. |
| 5,683,357 A | * | 11/1997 | Magram ................. A61M 1/70 604/9 |

(Continued)

FOREIGN PATENT DOCUMENTS

| | | |
|---|---|---|
| CA | 2994669 A1 | 2/2017 |
| CN | 105079891 A | 11/2015 |

(Continued)

OTHER PUBLICATIONS

International Search Report and Written Opinion dated Jun. 28, 2021 for International Application No. PCT/US2021/016401.

*Primary Examiner* — Leslie A Lopez
*Assistant Examiner* — Seth Han
(74) *Attorney, Agent, or Firm* — Seager, Tufte & Wickhem LLP (57) ABSTRACT

Systems, catheters, and methods for accessing and treating along the central nervous system are disclosed including sampling systems. An example sampling system may include a filter cassette designed to filter cerebrospinal fluid. The filter cassette may have an inlet region configured to be coupled to a catheter and configured to receive cerebrospinal fluid, one or more filters, and an outlet region configured to be coupled to an outlet of the catheter and to direct filtered cerebrospinal fluid to the catheter. A sampling port may be in fluid communication with the filter cassette. The sampling port may have a first end region configured to receive cerebrospinal fluid, a stopcock, a syringe port, and a second end region. The stopcock may be configured to shift between a first position where cerebrospinal fluid is directed from the first end region to the second end region and a second position where cerebrospinal fluid is directed from the first end region to the syringe port.

17 Claims, 6 Drawing Sheets

(58) Field of Classification Search
CPC ...... A61M 2205/128; A61M 2205/125; A61M 2205/126; A61M 2205/75; A61M 2210/0693; A61M 27/006
See application file for complete search history.

(56) References Cited

U.S. PATENT DOCUMENTS

| | | | |
|---|---|---|---|
| 9,744,285 B2 | 8/2017 | Heyes et al. | |
| 2002/0148468 A1* | 10/2002 | Valeij | A61M 16/205 128/204.23 |
| 2004/0024358 A1 | 2/2004 | Meythaler et al. | |
| 2009/0230043 A1* | 9/2009 | Heyes | A61M 1/1524 210/182 |
| 2010/0004588 A1* | 1/2010 | Yeh | A61M 1/3472 73/61.41 |
| 2010/0084326 A1 | 4/2010 | Takesawa | |
| 2014/0319079 A1* | 10/2014 | Leland | B01D 63/084 210/435 |
| 2015/0112246 A1 | 4/2015 | Palmerton et al. | |
| 2016/0361476 A1 | 12/2016 | Huang | |
| 2017/0035950 A1* | 2/2017 | Meyering | A61M 1/884 |
| 2019/0009014 A1* | 1/2019 | Chen | A61M 1/14 |
| 2019/0105475 A1 | 4/2019 | Lad et al. | |

FOREIGN PATENT DOCUMENTS

| | | | | |
|---|---|---|---|---|
| EP | 0117695 A2 | 9/1984 | | |
| JP | H11342209 | 12/1999 | | |
| JP | 2008539849 A | 11/2008 | | |
| JP | 2020536618 A | 12/2020 | | |
| WO | 2015131087 A1 | 9/2015 | | |
| WO | 2019071056 A1 | 4/2019 | | |
| WO | WO-2020068509 A1 * | 4/2020 | .......... A61M 1/0058 |

* cited by examiner

SYSTEMS, CATHETERS, AND METHODS FOR TREATING ALONG THE CENTRAL NERVOUS SYSTEM

CROSS REFERENCE TO RELATED APPLICATIONS

The present application claims the benefit of and priority to U.S. Provisional Patent Application Ser. No. 62/969,632, filed on Feb. 3, 2020, the entire disclosure of which is incorporated herein by reference.

TECHNICAL FIELD

The present disclosure relates to systems, catheters, and methods for treating along the central nervous system.

BACKGROUND

A wide variety of medical devices have been developed for medical use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. A sampling system is disclosed. The sampling system comprises: a filter cassette designed to filter cerebrospinal fluid, the filter cassette having an inlet region configured to be coupled to a catheter and configured to receive cerebrospinal fluid, one or more filters, and an outlet region configured to be coupled to an outlet of the catheter and to direct filtered cerebrospinal fluid to the catheter; a sampling port in fluid communication with the filter cassette; wherein the sampling port has a first end region configured to receive cerebrospinal fluid, a stopcock, a syringe port, and a second end region; and wherein the stopcock is configured to shift between a first position where cerebrospinal fluid is directed from the first end region to the second end region and a second position where cerebrospinal fluid is directed from the first end region to the syringe port.

Alternatively or additionally to any of the embodiments above, when the stopcock is in the first position, the cerebrospinal fluid is substantially blocked from the syringe port.

Alternatively or additionally to any of the embodiments above, when the stopcock is in the second position, the cerebrospinal fluid is substantially blocked from the second end region.

Alternatively or additionally to any of the embodiments above, the one or more filters include a tangential flow filter.

Alternatively or additionally to any of the embodiments above, further comprising a syringe releasably coupled to the syringe port.

Alternatively or additionally to any of the embodiments above, the sampling port is in fluid communication with the inlet region of the filter cassette.

Alternatively or additionally to any of the embodiments above, the sampling port is configured to receive cerebrospinal fluid from the inlet region of the filtering cassette.

Alternatively or additionally to any of the embodiments above, the sampling port is configured to receive unfiltered cerebrospinal fluid from the inlet region of the filtering cassette.

Alternatively or additionally to any of the embodiments above, the sampling port is in fluid communication with the outlet region of the filter cassette.

Alternatively or additionally to any of the embodiments above, the sampling port is configured to receive cerebrospinal fluid from the outlet region of the filtering cassette.

Alternatively or additionally to any of the embodiments above, the sampling port is configured to receive filtered cerebrospinal fluid from the outlet region of the filtering cassette.

Alternatively or additionally to any of the embodiments above, the sampling port is in fluid communication with a waste outlet.

A sampling system is disclosed. The sampling system comprises: a filter cassette designed to filter cerebrospinal fluid, the filter cassette having an inlet region configured to be coupled to a catheter and configured to receive cerebrospinal fluid, one or more filters, and an outlet region configured to be coupled to an outlet of the catheter and to direct filtered cerebrospinal fluid to the catheter; a sampling port in fluid communication with the outlet region; the sampling port having a first end region configured to receive filtered cerebrospinal fluid, a stopcock, a syringe port, and a second end region; and wherein the stopcock is configured to shift between a first position where filtered cerebrospinal fluid is directed from the first end region to the second end region and a second position where filtered cerebrospinal fluid is directed from the first end region to the syringe port.

Alternatively or additionally to any of the embodiments above, when the stopcock is in the first position, the filtered cerebrospinal fluid is substantially blocked from the syringe port.

Alternatively or additionally to any of the embodiments above, when the stopcock is in the second position, the filtered cerebrospinal fluid is substantially blocked from the second end region.

Alternatively or additionally to any of the embodiments above, the one or more filters include a tangential flow filter.

Alternatively or additionally to any of the embodiments above, further comprising a syringe releasably coupled to the syringe port.

A method for collecting a sample from a cerebrospinal fluid system is disclosed. The method comprises: withdrawing cerebrospinal fluid from a patient with a cerebrospinal fluid system; wherein the cerebrospinal fluid system includes: a filter cassette designed to filter cerebrospinal fluid, the filter cassette having an inlet region configured to be coupled to a catheter and configured to receive cerebrospinal fluid, one or more filters, and an outlet region configured to be coupled to an outlet of the catheter and to direct filtered cerebrospinal fluid to the catheter, a sampling port in fluid communication with the outlet region, wherein sampling port has a first end region configured to receive filtered cerebrospinal fluid, a stopcock, a syringe port, and a second end region, and wherein the stopcock is configured to shift between a first position where filtered cerebrospinal fluid is directed from the first end region to the second end region and a second position where filtered cerebrospinal fluid is directed from the first end region to the syringe port; and shifting the stopcock from the first position to the second position.

Alternatively or additionally to any of the embodiments above, when the stopcock is in the first position, the filtered cerebrospinal fluid is substantially blocked from the syringe port.

Alternatively or additionally to any of the embodiments above, when the stopcock is in the second position, the filtered cerebrospinal fluid is substantially blocked from the second end region.

Alternatively or additionally to any of the embodiments above, the one or more filters include a tangential flow filter.

Alternatively or additionally to any of the embodiments above, further comprising releasably attaching a syringe to the syringe port.

Alternatively or additionally to any of the embodiments above, releasably attaching a syringe to the syringe port includes releasably attaching the syringe to the syringe port prior to shifting the stopcock from the first position to the second position.

Alternatively or additionally to any of the embodiments above, shifting the stopcock from the first position to the second position directs filtered cerebrospinal fluid into the syringe.

Alternatively or additionally to any of the embodiments above, shifting the stopcock from the first position to the second position automatically directs filtered cerebrospinal fluid into the syringe.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAIL DESCRIPTION

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Cerebrospinal fluid (CSF) is a generally clear, colorless fluid with viscosity similar to water that is produced within the choroid plexus located in the ventricles of the brain. Total CSF volume has been estimated to range from approximately 150 to 300 milliliters in healthy adults. The choroid plexus is believed to produce approximately 500 milliliters of CSF daily in order to accommodate flushing or recycling of CSF to remove toxins and metabolites. The total volume of CSF is replenished several times per day or possibly more during sleep cycles and other activities. CSF also serves to float the delicate brain tissue by the Archimedes principle, and it protects the brain from sudden movements by cushioning the tissue. From the choroid plexus, CSF flows slowly through a series of openings into the space surrounding the brain and spinal column, and then into the body through multiple outflow pathways that include arachnoid granulations, cribiform plate, dural lymphatics, spinal cord nerve root sleeves, and possibly other pathways within the brain tissue. CSF is found in the space between the pia mater and the arachnoid mater, known as the subarachnoid space and also located within the ventricular system of the brain and in a series of cisterns located external to the brain. In addition to the net production and absorption of CSF flow, the CSF oscillates with a back-and-forth motion in synchrony with the cardiac and respiratory cycle. The magnitude of these oscillations is variable depending on the specific region of CSF. CSF flow can also be intermittently altered based on various maneuvers such as valsalva, coughing, sneezing, playing a musical instrument, and athletic activities. CSF pressure in a healthy adult is approximately 10 millimeters of mercury in the supine position. CSF pressure is altered in the standing position by hydrostatic pressure gradient along CSF system and can also be transiently affected by maneuvers such as coughing.

Research has indicated that alterations of the biochemical composition of CSF can be indicative and/or involved in the pathological processes of a plethora of central nervous system disease states. For example, in the event of a stroke or other brain trauma, blood can enter the CSF system leading to subsequent injury to the brain due to blood clotting and other biological processes. In context of amyotrophic lateral sclerosis, several chemicals (inflammatory proteins or cytokines such as CHIT1) have been found to be abnormally elevated potentially contributing to the disease pathology. Similarly, in multiple sclerosis proteins, cytokines and chemokines have been found to be elevated and potentially underlying disease progression. As such, in principle, it could be beneficial to remove CSF with abnormal biochemical composition; however, direct removal of CSF is limited as only relatively small amounts can be safely removed. Thus, it can be desirable to remove the CSF from one location (e.g., the cervical region of the spine, or a brain ventricle), alter it (e.g., filter), and return it to the CSF space at a second location (e.g., the lumbar region of the spine). This process can be used to remove the unwanted biochemical products while maintaining similar total CSF volume.

A process termed Neurapheresis may be understood to be the modification of materials (e.g. removal of microorganisms, cells, viruses, foreign material, drugs, combinations thereof, and the like, or circulation and/or addition of materials such as pharmacologic agents) from CSF. This and other therapeutic techniques can be used to treat a number of neurological diseases or conditions, such as Alzheimer's Disease, Parkinson's Disease, Huntington's Disease, Amyotrophic Lateral Sclerosis (ALS), Encephalitis from various causes, Meningitis from various causes, Guillain-Barré Syndrome (GBS), Multiple Sclerosis (MS), HIV-associated neurocognitive disorders, Spinal Cord Injury, Traumatic Brain Injury, cerebral vasospasm, stroke and other diseases or conditions. In addition, Neurapheresis can be used during open or endoscopic spine surgery or brain surgery, for example to remove blood that may get in the CSF during the surgery.

During a medical intervention such as Neurapheresis, it may be desirable to collect a sample of CSF. For example, it may be desirable to collect a sample of CSF in order to analyze the sample, quantify one or more substances (e.g., pathogens, prokaryotic organisms, eukaryotic organisms, viruses, contaminants, drugs, and/or the like) within the CSF, monitor drug levels within the CSF, monitor progress of a treatment, combinations thereof, and/or the like. Disclosed herein are systems that allow for a sample of CSF to be collected during an intervention.

Figure 1:
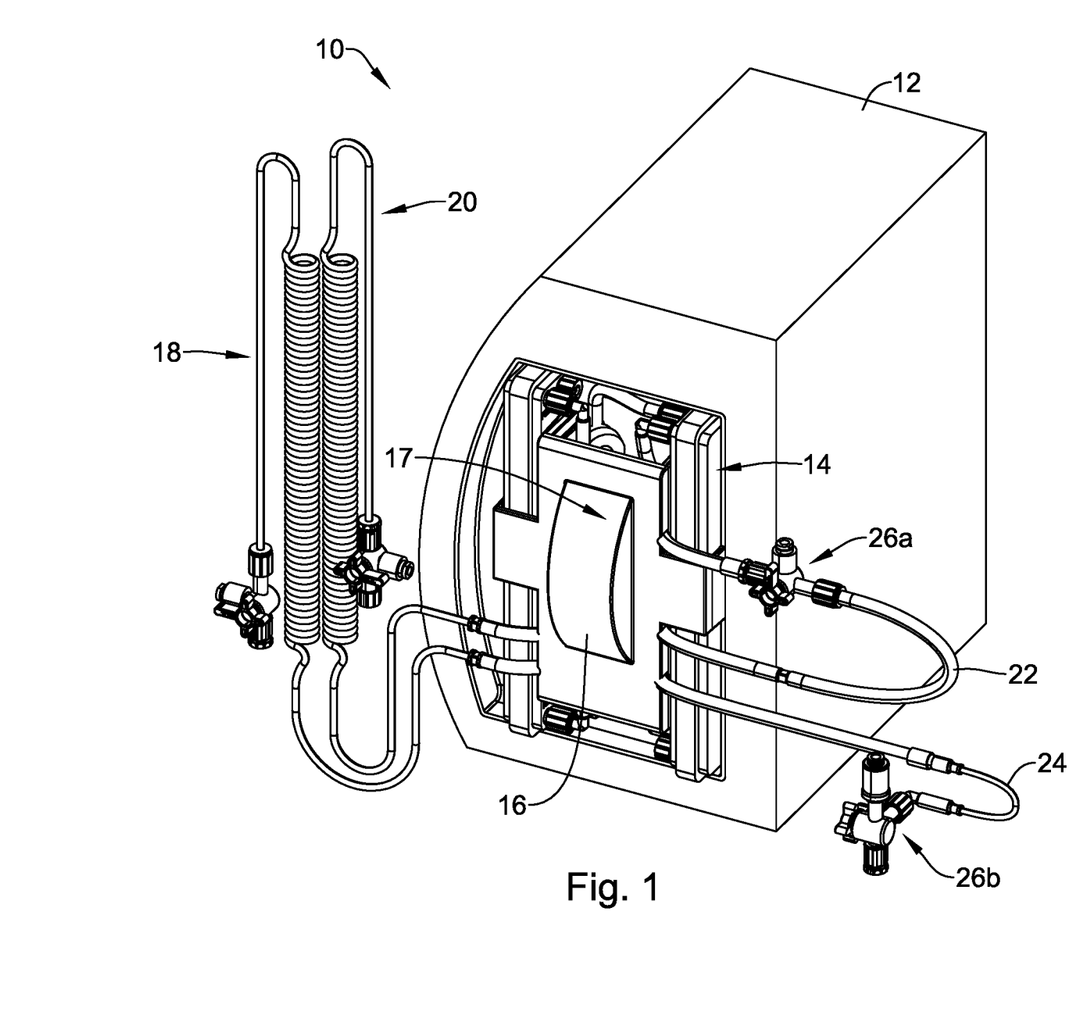
FIG. 1 is a perspective view of a portion of an example system.

FIG. 1 is a perspective view of a portion of an example system 10, for example a portion of a Neurapheresis system 10. The system 10 may include a controller assembly 12. The controller assembly 12 may include a socket or opening 14 designed to house a filtering member or cassette 16. In at least some instances, the filtering cassette 16 includes one or filters (e.g., such as tangential flow filters, dead-end filters, electrofilters, combinations thereof, and/or the like) generally designed to filter CSF. Tubing may be coupled to the filtering cassette 16. In some instances, the tubing may include an aspiration or inlet region 18 that may be coupled to the filtering cassette 16. The aspiration region 18 may be coupled to a catheter (not shown) and may define a pathway through which CSF can be removed from a patient and be processed/filtered by the filtering cassette 16. In some instances, the tubing may include a return or outlet region 20 that may be coupled to the filtering cassette 16. The return region 20 may be used to return CSF (e.g., filtered CSF) to the patient. The return region 20 may be coupled to a catheter (not shown) and may define a pathway through which processed/filtered CSF can be returned to the patient.

The tubing coupled to the filtering cassette 16 may also include a first pump region 22, for example, that may extend from the filtering cassette 16. The first pump region 22 may be designed to engage a pump head (not shown) so that CSF can be pumped/circulated through the filtering cassette 16 and, ultimately filtered CSF can be returned to the patient. The tubing coupled to the filtering cassette 16 may include a second pump region 24, for example, that may extend from the filtering cassette 16. The second pump region 24 may be designed to engage another pump head (not shown) so that waste material can be pumped from the pumping cassette 16.

In use, the system 10 may be used by coupling a catheter (not shown) to the system 10 and disposing the catheter within/along the cerebrospinal space (e.g., such as along lumbar cerebrospinal space). CSF may be removed/aspirated using the catheter and the removed CSF may be processed/filtered using the filtering cassette 16. The filtered/conditioned CSF may then be returned to the patient using the catheter.

The tubing may include one or more sampling ports, for example sampling ports 26a, 26b, generally disposed along the tubing of the filtering cassette 16. It can be appreciated that the position of a given sampling port may impact the type of CSF sample collected. For example, sampling port 26a may be disposed adjacent to the filtering cassette 16 and be in fluid communication with the aspiration region 18 such that samples collected at the sampling port 26a represent CSF collected directly from the patient (e.g., "unfiltered" or "untreated" CSF). Samples collected at the sampling port 26a, thus, may be used to analyze the CSF, quantify one or more substances (e.g., pathogens, prokaryotic organisms, eukaryotic organisms, viruses, contaminants, drugs, and/or the like) within the CSF, monitor drug levels in the CSF, monitor progress of a treatment, combinations thereof, and/or the like. The sampling port 26b may be disposed adjacent to the filtering cassette 16 such that waste material (e.g., material removed/filtered from CSF) can be collected and/or analyzed. Thus, the sampling port 26b may be understood to be in fluid communication with a waste outlet (e.g., a pathway from the filtering cassette 16 where the waste material is transported). The system 10 may include additional ports that allow for a clinician to assess the filtration during a Neurapheresis procedure. Such sampling ports may be disposed along or in fluid communication with the return region 20. For example, one or more additional sampling ports may be in fluid communication with the return region 20 such that samples collected at this sampling port represent filtered/treated CSF. Thus, collectively, sampling ports are contemplated that can be used to collect (a) unfiltered CSF, (b) filtered/treated CSF, and/or (c) waste material.

A representative sampling port 26, representative of any of the sampling ports (e.g., including the sampling ports 26a, 26b) of the system 10, is depicted in FIGS. 2-6. Here it can be seen that the sampling port 26 may include a first end region 32 configured to be coupled to an inlet region 34. The sampling port 26 may also include a second end region 28 configured to be coupled to an outlet region 30. In this example, the outlet region 30 is in fluid communication with the filter cassette 16. The sampling port 26 may also include a syringe port 36 configured to be coupled to a syringe 38. The syringe 38 may include a syringe barrel 40 and a plunger 42.

Figure 2:
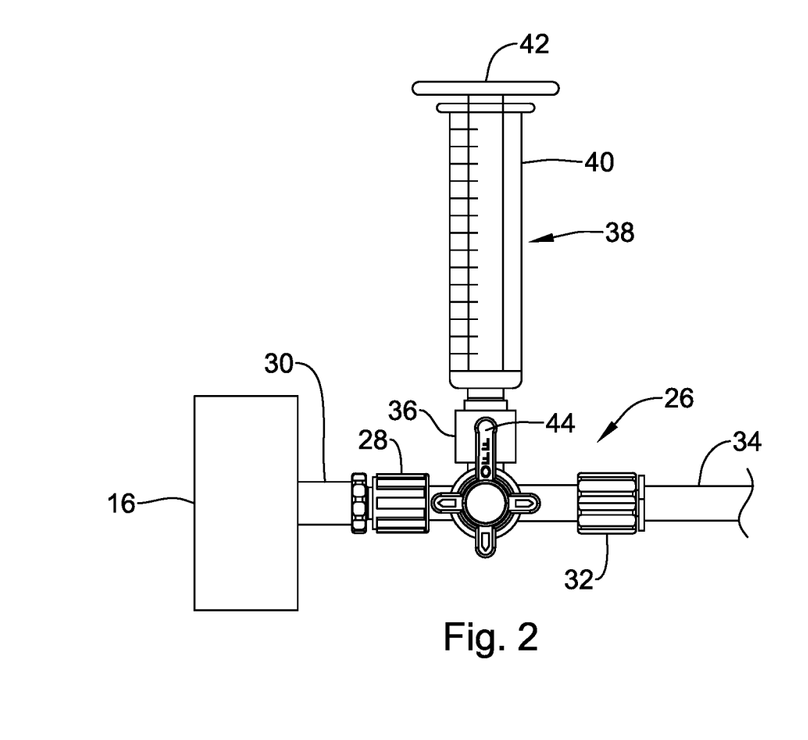
FIG. 2 is a side view of a portion of an example system.

A stopcock or valve 44 may be coupled to the sampling port 26. The stopcock 44 may be configured to shift between one or more positions or configurations. For example, when the stopcock 44 is in a first position (e.g., as shown in FIG. 2), CSF is directed from the first end region 32 to the second end region 28. In at least some instances, when the stopcock 44 is in the first position, CSF is substantially blocked from the syringe port 36.

Figure 3:
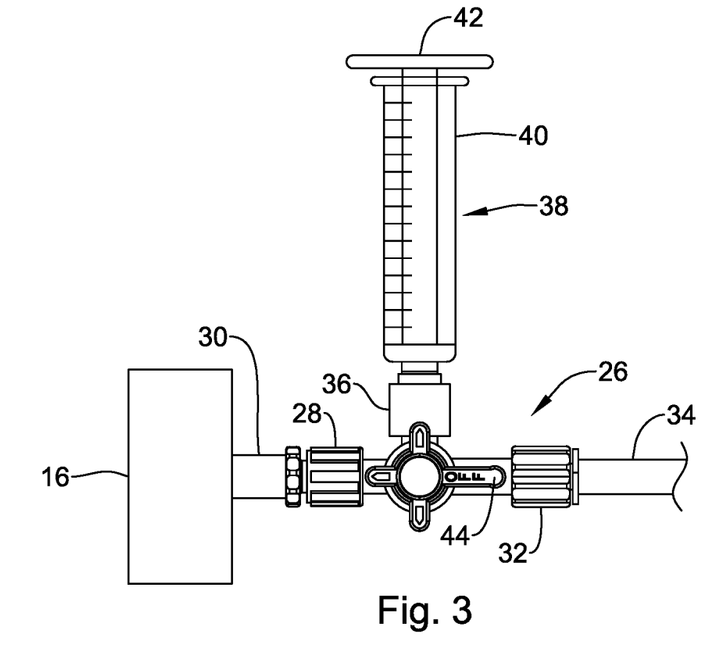
FIG. 3 is a side view of a portion of an example system.

When the stopcock 44 is shifted to or otherwise in a second position (e.g., as shown in FIG. 3), CSF is directed from the first end region 32 to the syringe port 36. In at least some instances, when the stopcock 44 is in the second position, CSF is substantially blocked from the second end region 28.

Figure 4:
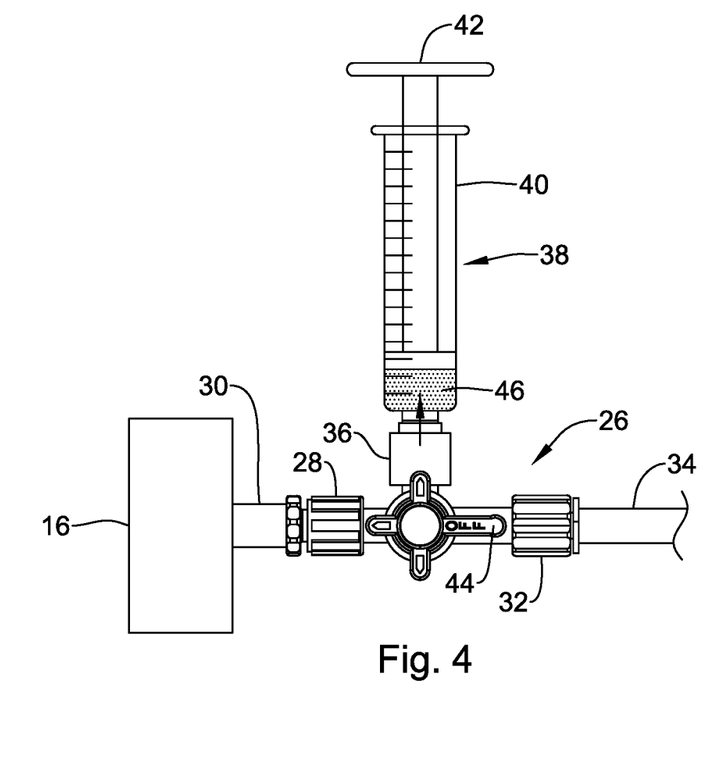
FIG. 4 is a side view of a portion of an example system.
Figure 5:
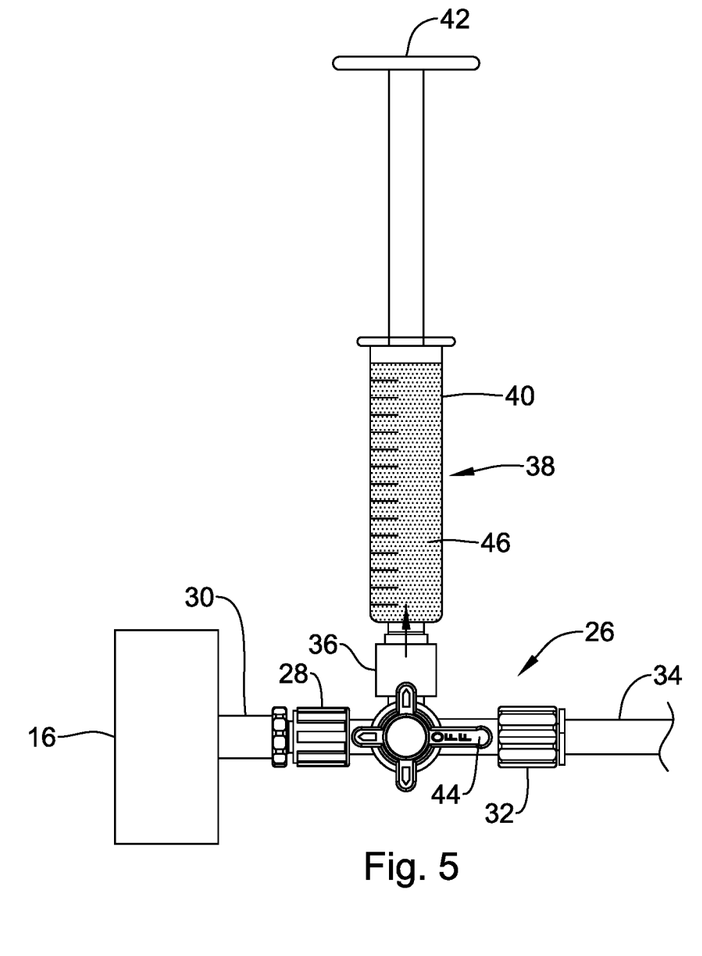
FIG. 5 is a side view of a portion of an example system.
Figure 6:
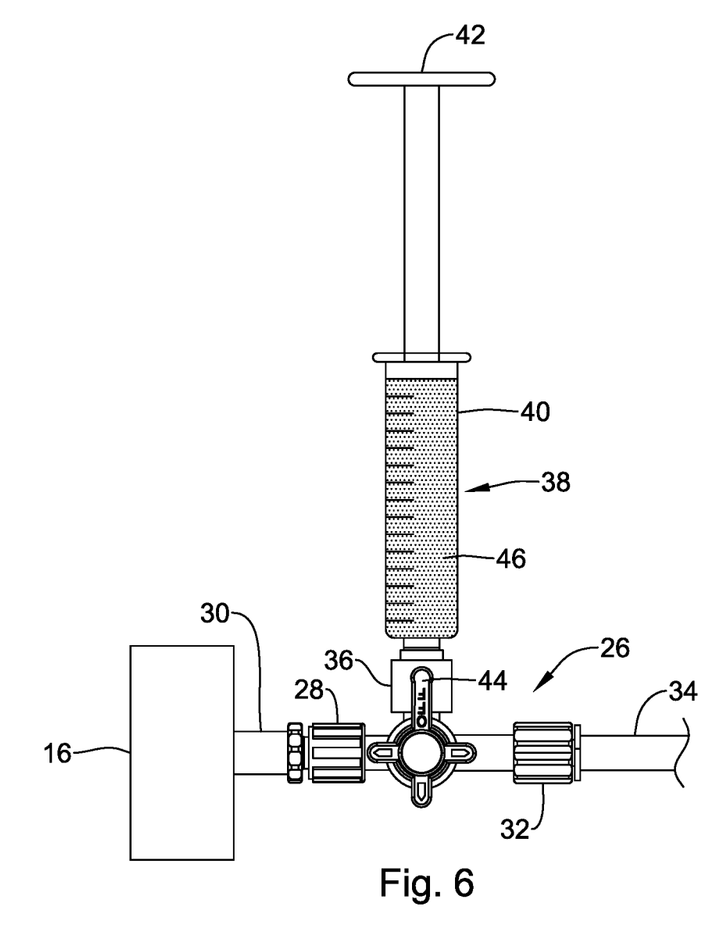
FIG. 6 is a side view of a portion of an example system.

When the stopcock 44 is in the second position, a sample 46 of CSF may flow into the syringe 38 as depicted in FIG. 4. When a sufficient amount of the sample 46 is collected, for example as depicted in FIG. 5, the stopcock 44 may be returned to the first position as shown in FIG. 6. As desired, the syringe 38 can be removed from the syringe port 36, for example so that the sample 46 can be analyzed/processed. It can be appreciated that in the example depicted in FIGS. 2-6, the sample collected in the syringe 38 may include unfiltered CSF. In other examples, similar to this example, the sample may include filtered/treated CSF or waste material. In these other example, the location of the sample port 28 may be suitable located.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A sampling system, comprising:
   a filter cassette designed to filter cerebrospinal fluid, the filter cassette having an inlet region configured to be coupled to a catheter and configured to receive cerebrospinal fluid, one or more filters, and an outlet region configured to be coupled to an outlet of the catheter and to direct filtered cerebrospinal fluid to the catheter;
   wherein the filter cassette is configured to be housed within an opening in a controller assembly;
   a cerebrospinal fluid sampling port in fluid communication with the inlet region and the outlet region of the filter cassette; and
   a waste sampling port in fluid communication with the filter cassette and a waste outlet, wherein the waste sampling port is disposed along tubing of the filtering cassette, and wherein the waste sampling port is configured to receive waste material that is filtered from the cerebrospinal fluid by the filter cassette;
   wherein the cerebrospinal fluid sampling port has a first end region configured to receive cerebrospinal fluid, a stopcock, a syringe port, and a second end region; and
   wherein the stopcock is configured to shift between a first position where cerebrospinal fluid is directed from the first end region to the second end region and a second position where cerebrospinal fluid is directed from the first end region to the syringe port.

2. The sampling system of claim 1, wherein when the stopcock is in the first position, the cerebrospinal fluid is substantially blocked from the syringe port.

3. The sampling system of claim 1, wherein when the stopcock is in the second position, the cerebrospinal fluid is substantially blocked from the second end region.

4. The sampling system of claim 1, wherein the one or more filters include a tangential flow filter.

5. The sampling system of claim 1, further comprising a syringe releasably coupled to the syringe port.

6. The sampling system of claim 1, wherein the cerebrospinal fluid sampling port is configured to receive cerebrospinal fluid from the inlet region of the filter cassette.

7. The sampling system of claim 1, wherein the sampling port is configured to receive unfiltered cerebrospinal fluid from the inlet region of the filtering cassette.

8. The sampling system of claim 1, wherein the sampling port is configured to receive cerebrospinal fluid from the outlet region of the filtering cassette.

9. The sampling system of claim 1, wherein the sampling port is configured to receive filtered cerebrospinal fluid from the outlet region of the filtering cassette.

10. A sampling system, comprising:
    a filter cassette designed to filter cerebrospinal fluid, the filter cassette having an inlet region configured to be coupled to a catheter and configured to receive cerebrospinal fluid, one or more filters, and an outlet region configured to be coupled to an outlet of the catheter and to direct filtered cerebrospinal fluid to the catheter;
    wherein the filter cassette is configured to be removably housed within a socket in a controller assembly;
    a waste sampling port in fluid communication with the filter cassette and a waste outlet, wherein the waste sampling port is disposed along tubing of the filtering cassette, and wherein the waste sampling port is configured to receive waste material that is filtered from the cerebrospinal fluid by the filter cassette;
    a cerebrospinal fluid sampling port in fluid communication with the inlet region and the outlet region;
    the cerebrospinal fluid sampling port having a first end region configured to receive the filtered cerebrospinal fluid, a stopcock, a syringe port, and a second end region; and
    wherein the stopcock is configured to shift between a first position where the filtered cerebrospinal fluid is directed from the first end region to the second end region and a second position where the filtered cerebrospinal fluid is directed from the first end region to the syringe port.

11. The sampling system of claim 10, wherein when the stopcock is in the first position, the filtered cerebrospinal fluid is substantially blocked from the syringe port.

12. The sampling system of claim 10, wherein when the stopcock is in the second position, the filtered cerebrospinal fluid is substantially blocked from the second end region.

13. The sampling system of claim 10, wherein the one or more filters include a tangential flow filter.

14. The sampling system of claim 10, further comprising a syringe releasably coupled to the syringe port.

15. A method for collecting a sample from a cerebrospinal fluid system, the method comprising:
    withdrawing cerebrospinal fluid from a patient with the cerebrospinal fluid system;
    wherein the cerebrospinal fluid system includes: a filter cassette designed to filter cerebrospinal fluid, the filter cassette having an inlet region configured to be coupled to a catheter and configured to receive cerebrospinal fluid, one or more filters, and an outlet region configured to be coupled to an outlet of the catheter and to direct filtered cerebrospinal fluid to the catheter,
    wherein the filter cassette is configured to be removably housed within an opening in a controller assembly; a waste sampling port in fluid communication with the filter cassette and
    a waste outlet, wherein the waste sampling port is disposed along tubing of the filtering cassette, and wherein the waste sampling port is configured to receive waste material that is filtered from the cerebrospinal fluid by the filter cassette;

a cerebrospinal fluid sampling port in fluid communication with the inlet and the outlet region, wherein the cerebrospinal fluid sampling port has a first end region configured to receive filtered cerebrospinal fluid, a stopcock, a syringe port, and a second end region, and wherein the stopcock is configured to shift between a first position where filtered cerebrospinal fluid is directed from the first end region to the second end region and a second position where unfiltered cerebrospinal fluid is directed from the first end region to the syringe port; and shifting the stopcock from the first position to the second position.

16. The method of claim 15, further comprising releasably attaching a syringe to the syringe port.

17. The method of claim 16, wherein shifting the stopcock from the first position to the second position automatically directs filtered cerebrospinal fluid into the syringe.

\* \* \* \* \*